(12) United States Patent
de Taboada

(10) Patent No.: US 7,703,153 B2
(45) Date of Patent: Apr. 27, 2010

(54) COMBINATION HAT AND SUNGLASSES/GOGGLES

(76) Inventor: Thierry Annez de Taboada, 5397 Nancy Greene Way, North Vancouver, BC (CA) V7R 4N2

( * ) Notice: Subject to any disclaimer, the term of this patent is extended or adjusted under 35 U.S.C. 154(b) by 228 days.

(21) Appl. No.: 11/850,308

(22) Filed: Sep. 5, 2007

(65) Prior Publication Data
US 2009/0056000 A1 Mar. 5, 2009

(51) Int. Cl.
*A42B 1/24* (2006.01)
(52) U.S. Cl. ............... 2/422; 2/12; 2/209.12; 2/175.1; 2/195.1
(58) Field of Classification Search .......... 2/422, 2/12, 209.12, 175.1, 195.1
See application file for complete search history.

(56) References Cited
U.S. PATENT DOCUMENTS
4,724,546 A * 2/1988 Cumbie, Jr. ............... 2/12

2002/0148033 A1 * 10/2002 Dufresne .................. 2/424

FOREIGN PATENT DOCUMENTS
| AU | 305992 S | 9/2005 |
| CA | 112633 | 10/2006 |
| EP | 318050-0001 | 5/2005 |

* cited by examiner

*Primary Examiner*—Gary L Welch
*Assistant Examiner*—Alissa J Tompkins
(74) *Attorney, Agent, or Firm*—Lang Michener LLP

(57) ABSTRACT

The present invention provides a combination hat and sunglasses/goggles, in which the sunglasses/goggles are pivotally moveable relative to the hat, between a raised, out of the way position to a lowered position with the eyepiece in front of the wearer's eyes, through an elongated aperture in the front brim of the hat. In addition, the sunglasses/goggles can be fully detached and removed from the hat, so that they can be used as regular sunglasses. The combination is easy to assemble and disassemble, and simple and convenient to operate, providing versatility and reduced risk of loss of components of the combination.

5 Claims, 2 Drawing Sheets

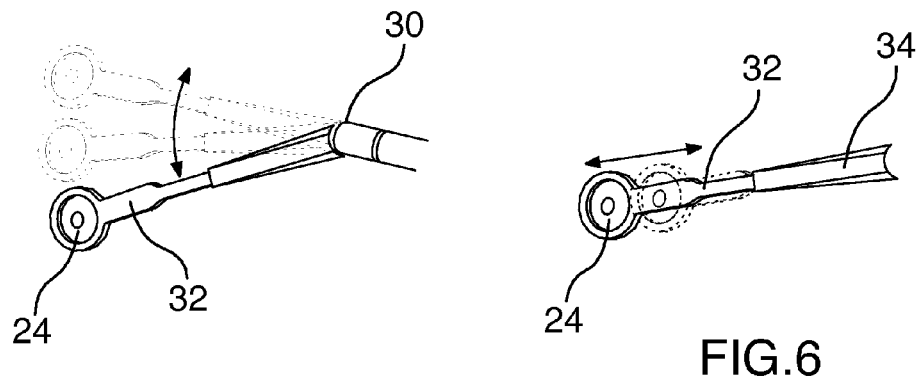
FIG.5
FIG.6
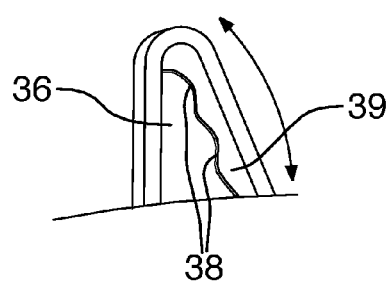
FIG.7
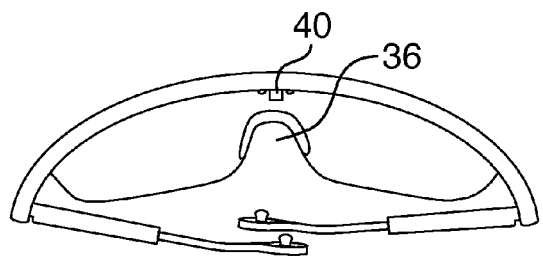
FIG.8
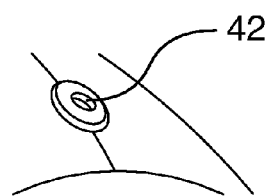
FIG.9

COMBINATION HAT AND SUNGLASSES/GOGGLES

FIELD OF THE INVENTION

This invention belongs to the field of personal head gear, and more particularly to the field of head gear for use in sunny conditions, providing a degree of protection for the wearer against potentially harmful exposure to direct sunlight.

BACKGROUND OF THE INVENTION

There are many different types and styles of sun hats available on the market. Likewise there are many different types of available sunglasses, providing more or less protection against the potentially harmful effects of sunlight on vision and the eye. Many users prefer to have both headgear protection and eye protection, i.e. sunglasses, when exposed to conditions of bright sunshine. This suggests a combination of a hat and sunglasses might be desirable. Such a combination is illustrated in Australian Registered Design 13999/2005 (AU-S-305992). On the other hand, many users prefer not to use sunglasses when there is no incident sunlight, with the result that, in intermittently sunny weather, users tend to want to remove and replace sunglasses at frequent intervals. This creates risk of losing or mislaying sunglasses. The same is not generally true of hats. Wearers of hats tend to keep them on for long periods of time, and do not have any wish to remove a hat in response to a brief interruption of sunshine.

Accordingly there is a need for a combination hat and sunglasses in which the sunglasses can be used and removed from use without interfering with the wearing of the hat.

BRIEF SUMMARY OF THE INVENTION

The present invention provides a combination hat and sunglasses/goggles, in which the sunglasses/goggles are pivotally moveable relative to the hat, between a raised, out of the way position to a lowered position in front of the wearer's eyes, as they are able to slide through an elongated aperture in the front brim of the hat. In addition, the sunglasses/goggles can be fully detached and removed from the hat, so that they can be used as regular sunglasses or goggles. The combination is easy to assemble and disassemble, and simple and convenient to operate, providing versatility and reduced risk of loss of components of the combination.

Thus according to the present invention, in one aspect, there is provided a combination hat and sunglasses/goggles for personal use, comprising a hat having a head receiving portion and a brim protruding from at least the front of the head receiving portion; an elongated aperture extending through the brim at the front of the head receiving portion; translucent sunglasses/goggles adapted to protrude through the elongated aperture and pivotally mounted on the head receiving portion of the hat, at two substantially diametrically opposed positions thereof; the sunglasses/goggles being pivotally moveable relative to the hat between a first position in which at least a major portion of the sunglasses/goggles is raised above the brim, and a second position in which at least a major portion of the sunglasses/goggles protrudes downwardly through the aperture below the brim, the sunglasses/goggles being detachable from and re-attachable to the head receiving portion of the hat.

DESCRIPTION OF THE PREFERRED EMBODIMENTS

Preferably the hat is of the peaked type, such as a baseball cap, where the brim is just a peak protruding from the front of the cap. The invention is however applicable to other types of hat having a brim, provided that the brim extends forwardly of the head receiving portion.

Preferably also, the pivotal connections of the sunglasses/goggles to the hat are provided by press studs (snap fasteners), which allow easy connection and disconnection and allow for relative pivotal movement of the parts when connected. The preferred form of the invention also allows the sunglasses/goggles to be connected to extend forwardly of the hat and rearwardly of the hat, so that the sunglasses/goggles can be operative to provide eye protection even when the user is wearing the baseball cap backwards.

In the preferred form of the invention, the sunglasses/goggles have a single, continuous eyepiece, and the brim of the hat has a single elongated aperture through which it can protrude. The eyepiece may be made of tough transparent plastic so as to function as safety goggles for the wearer.

Other features and advantageous items of the preferred embodiments of the invention will be apparent from the following specific description with reference to the accompanying figures of drawings.

BRIEF REFERENCE TO THE DRAWINGS

The accompanying drawings show, by way of illustrative example only, a specific preferred embodiment of the present invention, in which:

FIG. 5 is a detail of the area marked "A" on FIG. 1;

FIG. 6 is a detail of the area marked "B" on FIG. 2;

FIG. 7 is a detail of the area marked "C" on FIG. 1;

FIG. 8 is a perspective view of the sunglasses/goggles detached from the cap;

FIG. 9 is a detail of a portion of the rear of the cap.

In the drawings, like reference numerals denote like parts.

DETAILED DESCRIPTION OF THE MOST PREFERRED EMBODIMENT

Figure 1:
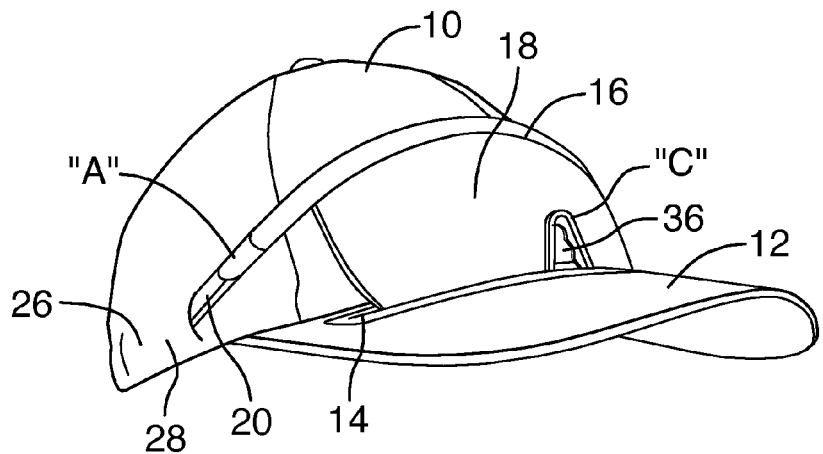
FIG. 1 is a perspective view of the hat-sunglasses/goggles visor combination of this embodiment in a first position, with a major portion of the eyepiece thereof raised above the peak of the cap.

With reference to FIG. 1 of the accompanying drawings, this illustrates a specific preferred form of the present invention, in which the hat portion of the combination is in the form of a baseball cap having a domed head receiving portion 10 and a peak 12 protruding from the front of the head receiving portion 10. A single, continuous elongated aperture 14 is provided in the peak 12, adjacent the head receiving portion 10. Sunglasses/goggles 16 are pivotally attached to the head receiving portion 10, at two substantially diametrically opposed positions.

Figure 2:
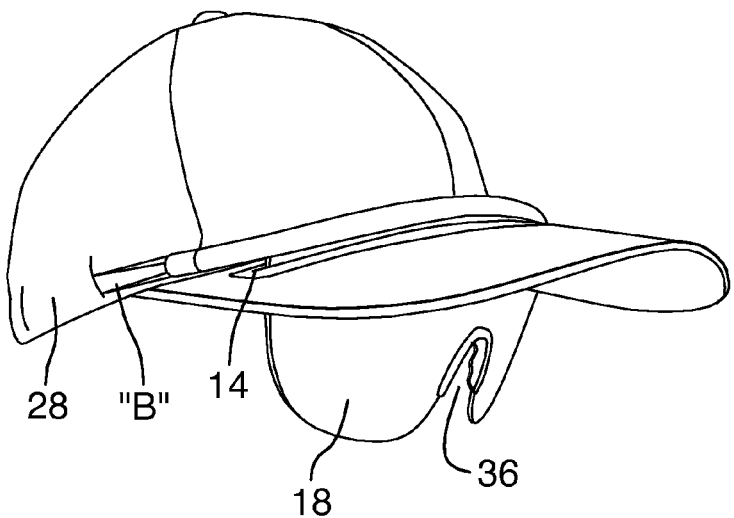
FIG. 2 is a similar perspective view, with the major portion of the eyepiece below the peak of the cap.

The sunglasses/goggles 16 have a single translucent eye piece 18 and a pair of opposed arms 20 and 22 pivotally attached thereto, in the manner of conventional sunglasses. The eyepiece is appropriately tinted and/or polarized to provide the user with eye protection from the sun. The sunglasses/goggles 16 are moveable from the position shown in FIG. 1, where the eyepiece 18 is largely above the peak 12, to a position shown in FIG. 2 where the eyepiece 18 protrudes through the aperture 14 into a position in front of the user's eyes. This movement is accomplished by pivoting of the arms 20, 22 about their end connections to the hat. For this purpose, the ends of the arms 20, 22 are each provided with a male press stud 24 (FIGS. 5 and 6), which releasably and pivotably engage respective female press studs 26 (FIG. 1) mounted on the head receiving portion 10 of the cap. Channels 28 are provided on each side of the cap, in which the female press studs are located. In fact there may be a plurality of female press studs 26 disposed in each channel, so that the sunglasses/goggles can be attached to the hat in different relative positions depending on the choice of female stud 26 to attach to male press stud 24. The press stud engagement arrangement allows for pivotal movement of the visor 16 relative to the hat, between the two positions shown in FIGS. 1 and 2.

The arms 20 and 22 are provided, between their attachment to the eyepiece 18 and their end press stud 24, with an articulation joint 30. This allows the angle of the eyepiece 18 to be varied, as shown in the detail drawing FIG. 5, where alternative positions are indicated in ghost. In this manner, eyepiece 18 can be moved closer to and further away from the user's face, as desired. Further, each of the arms 20, 22 is made of an end piece 32, carrying the male press stud 24 at its extremity and an intermediate piece 34 (FIG. 6) in which the end piece 32 is slidably received, so that the arms 20, 22 are telescopically adjustable in length.

The eyepiece 18 is provided on its lower edge with an upwardly extending recess 36 shaped to accommodate a user's nose. The sides of the recess 36 are provide with a series of indentations 38 (FIG. 7), and an outwardly protruding lower lip 39 so as to allow for different positioning of the eyepiece on the user's nose, and to hinder accidental complete removal of the sunglasses/goggles through the aperture.

Figure 3:
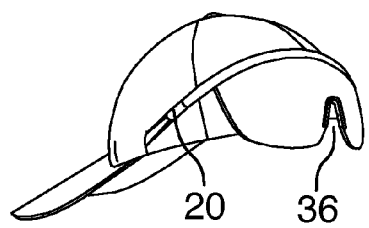
FIGS. 3 and 4 are views similar to those of FIGS. 1 and 2 respectively, showing the cap and sunglasses/goggles combination thereof in reverse mode.
Figure 4:
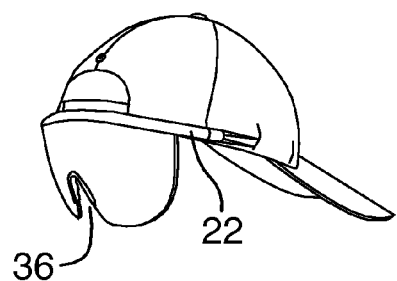

On occasion, a user wishes to wear a baseball cap backwards, so that the peak of the cap shields the wearer's neck from the sun. The illustrated embodiment of the invention permits the sunglasses/goggles to be releasably and pivotally mounted on the cap in the reverse position to allow the eyepiece to be used in the manner of sunglasses when the cap is worn backwards. This is illustrated in FIGS. 3 and 4. For this purpose, the channels 28 on the cap, within which the female press studs 26 are disposed, are open at both ends, front and back. This allows the arms 20, 22 to be inserted into the forward end of the slot to protrude forwardly, as in FIGS. 1 and 2, or into the rearward end of the slot to protrude rearwardly, FIGS. 3 and 4, when the cap is worn in the reverse position. Even when assembled in reverse, the sunglasses/goggles 16 is pivotable relative to the hat between a raised, out of the way position (FIG. 3) and a lowered position in which the eyepiece 18 is before the eyes (FIG. 4).

The sunglasses/goggles 16, when fully removed from the hat, have the basic features of a pair of sunglasses, as shown in FIG. 8. Thus the arms 20, 22 are foldable towards each other, to lie substantially parallel to and alongside the eyepiece 18, and the extremities of the arms can be folded out to rest on the ears of the user, with the recess 36 engaging the user's nose for use independently of the hat as sunglasses. Further, the sunglasses/goggles 16 are provided with an additional male press stud 40, at its central rear portion (FIG. 8) and the head receiving portion 10 of the hat is provided on its rear surface with a female press stud 42 (FIG. 9), so that the sunglasses/goggles can be releasably attached to the hat for storage purposes when its use is not required.

The illustrated embodiment of the invention is exemplary only, variations can be made within the scope of the invention. Thus, although the illustrated embodiment has an eyepiece in the form of a single continuous lens, as a visor, a pair of eyepieces resembling lenses could be provided instead. In such a case, the peak of the cap may have a pair of aligned elongated apertures instead of a single such aperture, through which the eyepieces protrude. Also, the eyepiece may be made of translucent toughened plastic, to function as safety goggles for the user. The eyepieces may be decorated with patterns, logos, slogans etc., as with some types of known sunglasses. The invention is limited only by the scope of the appended claims, fairly construed.

What is claimed is:

1. A combination hat and sunglasses/goggles for personal use, comprising:
    a hat having a head receiving portion and a brim protruding from at least the front of the head receiving portion, wherein the brim is constituted by a peak extending from the front only of the head receiving portion;
    an elongated aperture extending through the brim at the front of the head receiving portion;
    a translucent sunglasses/goggles adapted to protrude through the elongated aperture and pivotally mounted on the head receiving portion of the hat, at two substantially diametrically opposed positions thereof, wherein the sunglasses/goggles comprises an eyepiece and a pair of side arms protruding from upper lateral ends of the eyepiece, and wherein the side arms of the sunglasses/goggles are articulated in two substantially mutually perpendicular planes, to allow folding inwardly towards each other when the sunglasses/goggles are detached from the hat, and to allow pivoting of the eyepiece towards and away from the user's face when in use;
    the sunglasses/goggles being pivotally moveable relative to the hat between a first position in which at least a major portion of the sunglasses/goggles is raised above the brim, and a second position in which at least a major portion of the sunglasses/goggles protrudes downwardly through the aperture below the brim;
    the sunglasses/goggles being detachable from and re-attachable to the head receiving portion of the hat.

2. The combination of claim 1 wherein the eyepiece of the sunglasses/goggles includes an upwardly extending recess for engagement with a user's nose, the recess having a plurality of opposed lateral side indentations and an outwardly extending lip, to permit engagement with the user's nose in a plurality of positions relative thereto and to hinder accidental removal of the eyepiece completely through the aperture.

3. The combination of claim 2 wherein the head receiving portion of the hat includes channels within which the press studs are disposed, the channels having both front openings and rear openings allowing access of the ends of the side arms to connect thereto with the eyepiece extending either forwardly or rearwardly of the head receiving portion of the hat.

4. The combination of claim 1 further including press studs at the ends of the side arms of the sun visor, and press studs co-operable therewith on the head receiving portions of the hat, to provide pivotal, detachable connection of the sunglasses/goggles to the hat, and wherein the side arms are telescopic.

5. The combination of claim 1 including a press stud on the rear portion of the head receiving portion of the hat, and a press stud co-operable therewith on the center portion of the sun visor, for detachably mounting the sunglasses/goggles to the hat when not in use.

* * * * *